United States Patent
Stowell

(10) Patent No.: US 8,246,869 B2
(45) Date of Patent: Aug. 21, 2012

(54) PHOTO-RESPONSIVE MICROENCAPSULATION MATERIALS, COMPOSITIONS AND METHODS OF USE THEREOF

(75) Inventor: Michael H. B. Stowell, Boulder, CO (US)

(73) Assignee: Solarbre, Inc., Boulder, CO (US)

( * ) Notice: Subject to any disclaimer, the term of this patent is extended or adjusted under 35 U.S.C. 154(b) by 916 days.

(21) Appl. No.: 12/091,297

(22) PCT Filed: Oct. 30, 2006

(86) PCT No.: PCT/US2006/060351
§ 371 (c)(1), (2), (4) Date: Nov. 14, 2008

(87) PCT Pub. No.: WO2007/051198
PCT Pub. Date: May 3, 2007

(65) Prior Publication Data
US 2009/0202652 A1   Aug. 13, 2009

Related U.S. Application Data

(60) Provisional application No. 60/731,209, filed on Oct. 28, 2005.

(51) Int. Cl.
*B01J 13/02* (2006.01)
*B01J 13/06* (2006.01)
*B01J 13/16* (2006.01)
*C08G 63/60* (2006.01)

(52) U.S. Cl. ...... 264/4.1; 264/4.33; 264/4.7; 428/402.2; 428/402.21; 424/497; 524/599; 525/418; 528/271; 427/213.3; 427/213.34; 512/4

(58) Field of Classification Search .......... 264/4.1, 264/4.33, 4.7; 428/402.2, 402.24; 424/497; 524/599; 525/418; 528/271; 427/213.3, 427/213.34; 512/4
See application file for complete search history.

(56) References Cited

U.S. PATENT DOCUMENTS

| 4,001,216 | A | 1/1977 | Winkley et al. |
| 4,013,643 | A | 3/1977 | Nysted |
| 4,992,351 | A * | 2/1991 | Ohkuma et al. ............. 430/138 |
| 5,283,015 | A | 2/1994 | Hutchings et al. |
| 6,657,052 | B1 | 12/2003 | Tumbull |
| 2002/0050659 | A1 | 5/2002 | Toreki et al. |
| 2005/0158548 | A1 | 7/2005 | Senga |

FOREIGN PATENT DOCUMENTS
EP   0271979 A1   6/1988

OTHER PUBLICATIONS

Hansen, K.C., et al., "A Method for Photoinitiating Protein Folding in a Nondenaturing Environment," J. Am. Chem. Soc., 2000, 122:11567-11568.

Wildemann, H., et al., "A Short Olefin Metathesis-Based Route to Enantiomerically Pure Arylated Dihydropyrans and a,b-Unsaturated d-Valero Lactones," J. Org. Chem., 2003, 68:799-804.

* cited by examiner

*Primary Examiner* — James J Seidleck
*Assistant Examiner* — Saira B Haider
(74) *Attorney, Agent, or Firm* — McDonnell Boehnen Hulbert & Berghoff

(57) ABSTRACT

Photoactivatable prepolymers and methods of use thereof are disclosed for microencapsulation of a substantially water-insoluble material within a nonporous shell. As provided herein, the microencapsulated material is released with no more than a slow release rate. Upon exposure of the nonporous shell to light, the nonporous shell is converted into a porous shell having an increased release rate for the microencapsulated material.

8 Claims, No Drawings

PHOTO-RESPONSIVE MICROENCAPSULATION MATERIALS, COMPOSITIONS AND METHODS OF USE THEREOF

This is a 371 national phase application of PCT/US2006/060351 filed 30 Oct. 2006, claiming priority to U.S. Provisional Application No. 60/731,209 filed 28 Oct. 2005, the contents of which are incorporated herein by reference.

BACKGROUND OF THE INVENTION

A. Field of the Invention

This invention relates to microcapsules and to methods for making and using said microcapsules. In particular, this invention relates to microcapsules comprising encapsulated droplets of a liquid material that is substantially insoluble in water, where the encapsulating agent is a film formed from a polymer that includes one component that is photoactivatable. Photoactivation of the microcapsules results in partial or substantial loss of encapsulation properties of the encapsulating polymer and concomitant partial or substantial release of the encapsulated material following illumination of the microcapsules with light, including sunlight and ambient indoor light.

B. Description of the Related Art

The use of membranes, coatings, and capsules for the controlled release of liquid materials is well known in the chemical arts for both agricultural and non-agricultural chemicals. In agriculture, controlled-release techniques have improved the efficiency of herbicides, insecticides, fungicides, bactericides, and fertilizers. Non-agricultural uses include encapsulated dyes, inks, pharmaceuticals, flavoring agents, and fragrances.

The most common forms of controlled-release materials are coated droplets or microcapsules, which are coated solids including both porous and non-porous particles, and coated aggregates of solid particles. In some instances, a water-soluble encapsulating film is desired, which releases the encapsulated material when the capsule is placed in contact with water. Other coatings are designed to release the entrapped material when the coating is ruptured by external force.

Still further coatings are porous in nature and release the entrapped material to the surrounding medium by diffusion through the pores, typically at a slow rate. In addition to providing controlled release, such coatings also serve to facilitate the dispersion of water-immiscible liquids into water and water-containing media such as wet soil. Droplets encapsulated in this manner are particularly useful in agriculture, where water from irrigation, rain, and water sprays is frequently present A variety of processes for producing such capsules are known in the art.

U.S. Pat. Nos. 2,800,457 (Green et al., Jul. 23, 1957) and 2,800,458 (Green, Jul. 23, 1957) describe formation of capsules by phase separation from an aqueous solution through the coacervation of a hydrophilic colloid sol.

U.S. Pat. Nos. 4,046,741 (Scher, Sep. 6, 1977) and 4,140,516 (Scher, Feb. 20, 1979) disclose an interfacial polymerization process, whereby the film-forming reactants are dissolved in the hydrophobic liquid which is dispersed in water, the reaction occurring at the interface when the phases are placed in contact as an emulsion.

U.S. Pat. No. 3,726,804 (Matsukawa et al., Apr. 10, 1973) describes another interfacial polymerization process whereby all the film-forming ingredients initially reside in hydrophobic droplets which also contain a low boiling point or polar solvent in addition to the material to be encapsulated. Upon heating, the solvent is released into the aqueous phase (the continuous phase of the emulsion), and the film-forming materials accumulate at the interface and polymerize.

Olefin polymerization using a peroxide catalyst is described in Japanese patent publication No. 9168/1961, whereby an oil-insoluble polymer is formed at the surfaces of oil drops.

British Patent Nos. 952,807 and 965,074 describe a process whereby a solid such as wax or a thermoplastic resin is melted, dispersed and cooled to form an encapsulating film around liquid droplets.

U.S. Pat. No. 3,111,407 (Lindquist et al., Nov. 19, 1963) describes a spray-drying method which form-s encapsulated droplets at the instant of atomization.

These processes vary in terms of equipment expense, energy requirements, ease of controlling microcapsule size, the need for extra reagents such as catalysts and settling agents, and percent microcapsule phase. In addition, the type of prepolymers utilized in these processes results in different release properties of the microencapsulated materials. Moreover, the art teaches microcapsules that release their contents under restrictive conditions (contact with water or mechanical rupture) that are not appropriate or advantageous for all applications. There is therefore a need in the art for microcapsules and methods for producing microcapsules that release the entrapped material under less restrictive conditions, particularly upon simple exposure to electromagnetic radiation, preferably common sunlight and/or room light.

SUMMARY OF THE INVENTION

The invention provides microcapsules and methods for making said microcapsules wherein a liquid material that is substantially insoluble in water can be microencapsulated within a nonporous shell that can be converted into a porous shell that releases the liquid material upon exposure to light, most particularly sunlight or ambient indoor lighting.

The invention provides methods for producing microcapsules encompassing said substances, comprising the steps of:
(a) providing an organic solution comprising a substance to be encapsulated, most preferably a water-insoluble or immiscible substance, and further comprising an etherified prepolymer dissolved therein, wherein from about 1% to about 100% of the prepolymer material is a photoactivatable prepolymer;
(b) creating an emulsion of said organic solution in an continuous phase aqueous solution comprising water and a surface-active agent, wherein said emulsion comprises discrete droplets of said organic solution dispersed in said continuous phase aqueous solution, there being formed thereby an interface between the discrete droplets of organic solution and the surrounding continuous phase aqueous solution; and
(c) causing in situ self-condensation and curing of said prepolymers in the organic phase of said discrete droplets adjacent to said interface by a method including but not limited to heating, pH changes, and free radical initiation, wherein the microcapsules are allowed a sufficient period of time for substantial completion of in situ condensation of said prepolymers to convert the liquid droplets of said organic solution to microcapsules.

The resulting microcapsules are characterized by having solid, mostly impermeable polymer shells enclosing said liquid material. In preferred embodiments, the photoactivatable prepolymer is a benzoin derivative. In certain alternative embodiments, the photoactivatable prepolymer is an o-nitrobenzoyl derivative, an alpha-keto ester, a benzophenone, a benzyl alcohol, a phenacyl ester, a fluorenecarboxylate, an arylamine, a cinnamyl ester, or a vinylsilane, or combination thereof. The total percentage of prepolymers (photoactivatable and otherwise) in said organic solution preferably comprises from about 1% to about 70% of the organic solution on a weight basis.

The invention further provides microcapsules formed by this process, comprising a substantially water-insoluble liquid material. In particular embodiments, the substantially water-insoluble liquid material comprises one or a plurality of a fragrance, a drug, an herbicide or a pesticide.

The microcapsules provided by the invention advantageously are capable of effecting a slow rate or no rate of release (i.e., substantially equivalent to about 0 ppm/min) of the encapsulated liquid by diffusion through the nonporous shell to the surrounding medium, and can be converted to a porous shell by exposure of electromagnetic radiation, particularly ambient indoor light or sunlight. Conversion of the nonporous shell to a porous shell advantageously permits release of the encapsulated liquid at a higher rate (i.e., greater than about 0 ppm/min), particularly an effective rate for any particular encapsulated substance, wherein the release is achieved in an easily controlled and available manner, i.e. upon exposure to electromagnetic radiation, preferably sunlight or ambient indoor light.

Release of the liquid from the microcapsules of the invention preferably occurs by diffusion, the rate of which is affected by the porosity of the polymeric shell, which in turn is a property of the mixture of prepolymers used in forming the microcapsules. In particular the release rate is directly determined by the ratio of non-photoactivatable prepolymers and photoactivatable prepolymers used to form the particles. The rate of release is directly proportional to the porosity of the polymeric shell and can vary from 0 ppm/minute for completely nonporous shells to 100 ppm/minute or more for highly porous and photoconverted polymeric shells.

Specific preferred embodiments of the invention will become evident from the following more detailed description of certain preferred embodiments and the claims.

DESCRIPTION OF THE PREFERRED EMBODIMENTS

This invention provides microcapsules in which is encapsulated one or a plurality of substantially water-insoluble liquid materials, particularly comprising one or a plurality of a fragrance, a drug, a herbicide or a pesticide, although encapsulation of any substantially water-insoluble liquid material is contemplated as falling within the scope of the invention. As disclosed herein, the invention can be readily adapted to accommodate variations in the materials used, the kind of product desired, and other features that affect the efficiency, cost, or efficacy of the resulting microcapsules (it being recognized by those skilled in the art that the components of the microcapsules of the invention can be selected in alternative embodiments depending on the requirements of any particular embodiment of the microcapsules of the invention.). As the following disclosure indicates, both essential and optional features of the process and the product thereof can be varied over a wide range and remain within the scope of the invention.

As used herein, the term "photoactivatable" is intended to mean that the porosity of a microcapsule is increased upon exposure to electromagnetic radiation, most particularly ambient indoor light or sunlight This is achieved by chemical bond cleavage that is facilitated by the photoactivatable polymer materials. Upon exposure to light a photochemical rearrangement occurs which results in chemical bond cleavage in a bond or a multiplicity of bonds in polymers comprising the microcapsule. The result of chemical bond cleavage is to decrease the rigidity and increase the porosity of the microcapsule. As used herein, the term "biomolecule" is intended to encompass peptides, lipids, nucleic acids and carbohydrates.

A. Core Liquid

In certain embodiments, the organic solution that forms the interior of the capsules (defined herein as "the core liquid") is advantageously substantially insoluble or immiscible in water. In addition, however, even substantially water soluble materials can be used in producing the microcapsules of the invention. Preferably the organic solution may consist of a single liquid material or one or more active liquid or solid materials dissolved in an inert solvent that has at most a slight solubility in water. In the latter case, the liquid or solid solute must reside preferentially in the organic phase when the two phases are in equilibrium.

A wide variety of core liquids can be encapsulated by the methods of this invention, and are provided as microencapsulated embodiments of said liquid materials that can be released from the microcapsules by illuminating them with electromagnetic radiation, preferably sunlight or ambient indoor light. The most useful core liquids are those that do not react with the prepolymers, or any of the other components used in preparing the microcapsules. Thus, any nonreactive core liquid that will not diffuse through the polymeric shell membrane in the absence of light activation is suitable for use with the inventive methods. The core liquid can be a single chemical compound or a mixture of two or more compounds, and can also advantageously provide a solvent for dissolution of a water-insoluble or slightly soluble solute. The core liquid material encapsulated in the microcapsules of the invention can in specific embodiments diffuse into water, soil, air, or any other surrounding medium, as a liquid or by evaporation. Core liquid compounds suitable for encapsulation include chemical or biological agents such as solvents, drugs, fragrances, odors, flavors, herbicides, insecticides, fungicides, nematocides, bactericides, rodenticides, molluscides, acaricides, larvicides; animal, insect, and bird repellents; plant growth regulators; fertilizers; pheromones, sex lures and attractant compositions, as well mixtures of such agents. The microcapsules of this invention are particularly well adapted to fragrances for the cosmetic industry, including esters and alcohols. The following are examples of compounds that can be utilized in the present invention but the invention is not limited to these compounds:

Solvents

Particular embodiments of solvents useful for preparing microencapsulated embodiments thereof according to the methods of the invention, wherein the solvent is released from the microcapsule upon illumination with electromagnetic radiation, preferably sunlight or ambient indoor light, include but are not limited to ethers, pentanes, hexanes, acetone, and alcohols, preferably lower alcohols including for example ethanol, methanol, and hexanol.

Fragrances

Particular embodiments of fragrances useful for preparing microencapsulated embodiments thereof according to the methods of the invention, wherein the fragrance is released from the microcapsule upon illumination with electromagnetic radiation, preferably sunlight or ambient indoor light, include but are not limited to Allyl Amyl Glycolate, Amyl Cinnamic Aldehyde, Amyl Phenyl Acetate, Amyl Salicylate, Andrane, Aphermate, Benzyl Butyrate, Benzyl Propionate, Benzyl Salicylate, Bicyclononalactone, Canthoxal, Cedrenyl Acetate, Celestolide, Cinnamalva, Citral Dimethyl Acetal, Citronalva, Citronellol Coeur, Citronellyl Acetate, Citronellyl Formate, Clarycet, Clonal, Coniferan, Cyclabute, Cyclobultanate, Cyclohexyl Ethyl Acetate, Cyclolhexyl Ethyl Alcohol, Decyl Methyl Ether, Delta Damascone, Dihydro Cyclacet, Dihydro Floralate, Dihydro Floralol, Dihydro Myrcenyl Acetate, Dihydro Terpineol, Dihydro Terpinyl Acetate, Dimethyl Benzyl Carbiniol, Dimethyl Benzyl Carbinyl Acetate, Dimethyl Benzyl Carbinyl Butyrate, Dimethyl Cyclormol, Dimethyl Octanol, Dimethyl Phenyl Ethyl Carbinyl Acetate, Dimyrcetol, Diola, Ethyl Ortho Methoxy Benzoate, Ethyl Phenyl Glycidate, Fleuramone, Fleuranil, Floralate, Floralol, Floralozone, Fructone, Galbanum Coeur, Gelsone, Geraldehyde, Geraniol, Geranyl Acetate, Hexalon, Hexenyl Salicylate, Hexyl Acetate, Hexyl Cinnamic Aldehyde, Hexyl Salicylate, Hydroxyol, Indolarome, Intreleven Aldehyde, Intreleven Aldehyde, Ionone, Ionone Alpha, Ionone, Iso Amyl Butyrate, Iso Amyl Salicylate, Iso Bornyl Propionate, Iso Butyl Phenyl Acetate, Iso Butyl Quinoline, Iso Cyclemone E, Iso Cyclo Citral, Iso Cyclo Geraniol, Isoproxen, Lemsyn, Lyrame, Maritima, Methyl Anthranilate, Methyl Cedryl Ketone, Methyl Cinnamic Aldehyde alpha, Methyl Ionone Gamma A, Methyl Ionone Gamma Coeur, Methyl Ionone Gamma Pure, Methyl Lavender Ketone, Muguesia, Muguet Aldehyde, Myrac Aldehyde, Myrcenol, Myrcenyl Acetate, Neoproxen, Ocimene, Ocimenyl Acetate, Octacetal, Orivone, Oxaspirane, Ozofleur, Peomosa, Phenoxyethyl Iso Butyrate, Phenoxyethyl Propionate, Phenyl Ethyl Acetate, Phenyl Ethyl Alcohol, Phenyl Ethyl Benzoate, Phenyl Ethyl Formate, Phenyl Ethyl Iso Butyrate, Phenyl Ethyl Phenyl Acetate, Phenyl Ethyl Salicylate, Piconia, Precyclemone B, Prenyl Acetate, Proflora, Pseudo Linalyl Acetate, Rosalva, Rosamusk, Roseate, Rosemarel, Salicynalva, Sanjinol, Sandalwood Spirodecane, Styralyl Propionate, Syvertal, Terpineol, Terpinyl Acetate, Tetrahydro Muguol, Tetrahydro Myrcenol, Tetrameran, Tobacarol, Vanoris, Verdol, and Vigoflor.

Flavorings

Particular embodiments of flavors and flavorings useful for preparing microencapsulated embodiments thereof according to the methods of the invention, wherein the flavor or flavoring is released from the microcapsule upon illumination with electromagnetic radiation, preferably sunlight or ambient indoor light, include but are not limited to 4,5-Dimethyl-2-ethyl-3-thiazoline, 6-Methyl Coumarin, Allyl Caproate, Anethole, Asafoetida Oil, Black Pepper Oil, Buchu Sulfur Fractions, Butyric Acid, Cardamom Oil, Cassia Oil, Cassia Oil, Cinnamon Bark Oil, Cinnamon Leaf Oil, Clove Bud Oil, Clove Leaf Oil, Cocoa Distillate, Cocoa Essence Dark, Cocoa Essence White, Coffee Extract, Coriander Oil, Cyclodithalfarol, delta Decalactone, Dimethyl Benzyl Carbinyl Butyrate, Dimethyl Sulfide, Dithione, Ethyl-2-Methyl Butyrate, Ethyl-3-Hydroxy Butyrate, Ethyl Butyrate, Ethyl Iso Butyrate, Ethyl Iso Valerate, Ethyl Oxanoate, Eucalyptus Oil, Farnesene, Furfurrole, gamma-Decalactone, gamma-Hexylactone, gamma-Octalactone, gamma Dodecalactone, Ginger Oil, Grapefruit, Heptan-2-One, Hexene-3-One-4, Hexyl Acetate, Homo Cyclocitral, Honey Distillate, Ionone Beta, Iso Amyl Iso Valerate, Iso Butyl Caproate, Iso Butyl Furyl Propionate, Iso Fragarone, Isovaleric Acid, Juniperberry Oil, Ketone Mix, Lemon Oil, Lime Oil, Linalool, Linalyl Acetate, Mangone, Methional, Methyl Butyric Acid, Methyl Ketones, Methyl Oxycyclosulfide, Mushroom Extract, Cocoa Butter Distillate, Peanut Distillate, Nonan-2-One, Nutmeg Oil, Octanal, Octen-4-one-2, Olibanum, Orange Oil, Peach Flavor, Peppermint Oil, Phenyl Ethyl 2-Methyl Butyrate, Phenyl Ethyl Acetate, Phenyl Ethyl Alcohol, Phenyl Oxaromate, Pimento Berry Oil, Pimento Leaf Oil, Pineapple Compound, Popcorn Chemical, Propionic Acid, Raspberry Flavor, Schinus Molle Oil, Sclareolide, Sesame Distillate, Sinensals, Succinic Acid, trans-2-Hexenal, Trimenal Acetate, and Undecan-2-One.

Moisturizers, Humectants and Skin Product Additives

Particular embodiments of cosmetic products and components of cosmetics, including moisturizers, humectants and skin products additives useful for preparing microencapsulated embodiments thereof according to the methods of the invention, wherein the cosmetic product is released from the microcapsule upon illumination with electromagnetic radiation, preferably sunlight or ambient indoor light, include but are not limited to Alpha Hydroxy Acid, Camphor, Ceramides, Ellagic Acid, Glycerin, Glycine, Glycogen, Glycolic Acid, Hyaluronic Acid, Hydroquinone, Isopropyl, Isostearate, Isopropyl Palmitate, Kojic Acid, Lactic Acid, Lanolin, L-Ergothioneine, Licorice Extract, Linoleic Acid, Lysine, Octyl Methoxycinnamate, Octyl Palmitate, Oxybenzone, PABA (Para-Aminobenzoic Acid), Panthenol, Proline, Resveratrol, Retinol, Retinyl Palmitate, Salicylic Acid, Sorbic Acid, Sorbitol, Triclosan, Tyrosine, Vitamin A, Vitamin B, Vitamin C, Vitamin D, Vitamin E, and Witch Hazel.

Herbicides

Particular embodiments of herbicides useful for preparing microencapsulated embodiments thereof according to the methods of the invention, wherein the herbicide is released from the microcapsule upon illumination with electromagnetic radiation, preferably sunlight or ambient indoor light, include but are not limited to S-ethyl-N-cyclohexyl-N-ethylthiocarbamate, S-ethylhexyhydro-1H-azepine-1-carbothioate, S-2,3-dichloroallyl di-isopropylthiocarbamate, S-2,3,3-trichloroallyl di-isopropylthiocarbamate, S-ethyl dipropylthiocarbamate, S-4-chlorobenzyl diethylthiocarbamate, S-ethyl diisobutylthiocarbamate, S-benzyl di-sec-butylthiocarbamate, S-propyl dipropylthiocarbamate, S-propyl butylethylthiocarbaxate, N,N-diallylchloroacetamide, alpha.-chloro-6'-ethyl N-(2-methoxy-1-methylethyl)-acetanilide, N-butoxymethyl-alpha.-chloro-2',6'-diethylacetanilide, S—(O,O-diisopropyl phosphorodithioate) ester of N-(2-mercaptoethyl)benzenesulfonamide, N-benzyl N-isopropyltrimethylacetamide, 2-chloroallyl diethyldithiocarbamate, 2-sec-butyl-4,6-dinitrophenol,2,6-dinitro-N,N-dipropylcumidine,N-(cyclopropylmethyl)-.alpha.,.alpha.,-trifluoro-2,6-dinitro-N-propyl-p-toluidine, and 2-(1,2-dimethylpropylamino)-4-ethyl-amino-6-methylthio-1,3,5-triazine-2-ethyl-5-methyl-5-(2-methylbenzyloxy)-1,3-dioxane.

Insecticides

Particular embodiments of insecticides useful for preparing microencapsulated embodiments thereof according to the methods of the invention, wherein the insecticide is released from the microcapsule upon illumination with electromagnetic radiation, preferably sunlight or ambient indoor light, include but are not limited to S-tert-butylthiomethyl O,O-diethyl phosphorodithioate, O,O-diethyl-O-4-methylsulphinylphenyl phosphorothioate, O,O-diethyl O-2-isopropyl-6-methylpyrimidin-4-yl phosphorothioate, O,O-diethyl S-2-ethylthioethyl phosphorodithioate, S-chloromethyl O,O-diethyl phosphorodithioate, O-ethyl S,S-dipropyl phosphorodithioate, O,O,-diethyl S-ethylthiomethyl phosphorodithioate, O-(4-bromo-2-chlorophenyl) O-ethyl-S-propyl phosphorodithioate, S-1,2-di(ethoxycarbonyl)ethyl O,O-dimethylphosphorodithioate, O,O,O',O'-tetraethyl S,S'-methylene di(phosphorodithioate), O-(4-bromo-2,5-dichlorophenyl) O,O-diethyl phosphorothioate, S-4-chlorophenylthiomethyl O,O-diethyl phosphorodithioate, 2-chloro-1-(2,4-dichlorophenyl)vinyl diethyl phosphate, O-2,5-dichloro-4-(methylthio)phenyl O,O-diethyl phosphorodithioate, O-4-cyanophenyl O,O-dimethyl phosphorothioate, O,O dimethyl O-2-methylthioethyl phosphorothioate, O,O-diethyl O-2-ethylthioethyl phosphorothioate, O-2,4-dichlorophenyl O,O-diethyl phosphorothioate, O-2,4-dichlorophenyl O-ethyl phenylphosphonothioate, O,O-diethyl O-5-phenylisoxazol-3-yl-phosphorothioate, 1,3-di(methoxycarbonyl)-propen-2-yl dimethyl phosphate S,S'-(1,4-dioxane-2,3-diyl) O,O,O'O'-tetraethyl di(phosphorodithioate), O,O-dimethyl-O-4-nitro-m-tolyl phosphorothioate, O,O-dimethyl O-4-methylthio-m-tolyl phosphorothioate, O-(5-chloro-1-isopropyl-1,2,4-triazol-3-yl) O,O-diethylphosphorothioate, S-2-isopropylthioethyl O,O-dimethyl phosphorodithioate, 4-(methylthio)phenyl dipropyl phosphate, 1,2-dibromo-2,2-dichloroethyl dimethyl phosphate, O,O-diethyl-alpha.-cyanobenzylideneaminooxyphosphonothioate, O,O-diethyl O-4-nitrophenyl phosphorothioate, O-2-diethylamino-6-methylpyrimidin-4-yl O,O-diethyl phosphorothioate, O-2-diethylamino-6-methylpyrimidin-4-yl O,O-dimethyl phosphorothioate, (E)-O-2-isopropoxycarbonyl-1-methylvinyl O-methylethylphosphoramidothioate, O,O,O',O'-tetraethyldithiopyrophosphate, O,O,O',O'-tetramethyl-O,O'-thiodi-p-phenylenediphosphorothioate, S-2-ethylthioethyl-O,O-dimethylphosphorodithioate, O,O-diethyl-O-1-phenyl-1,2,4-triazol-3-ylphosphorothioate, O-ethyl O-2,4,5-trichlorophenyl ethylphosphonothioate, (+−)-3-allyl-2-methyl-4-oxocyclopent-2-enyl-(+)-cis,trans-chrysanthemate, (+−)-3-allyl-2methyl-4-oxocyclopent-2-enyl-(+)-trans-chrysanthemate, 3-phenoxbenzyl-(+−)-cis, transchrysanthemate, pyrethrins-2-(2-butoxyethoxy) ethylthiocyanateisobornyl-thiocyanoacetate, carbon disulfide 2-(4-tert-butylphenoxy)cyclohexyl prop-2-ynyl sulphite, 4,6-dinitro-6-octylphenylcrotonates, and ethyl 4,4'-dichlorobenzilate.

Defoliants

Particular embodiments of a defoliant useful for preparing microencapsulated embodiments thereof according to the methods of the invention, wherein the defoliant is released from the microcapsule upon illumination with electromagnetic radiation, preferably sunlight or ambient indoor light, include but are not limited to S,S,S-tributylphosphorotrithioate, tributyl phosphorotrithioite.

Fungicides

Particular embodiments of a fungicide useful for preparing microencapsulated embodiments thereof according to the methods of the invention, wherein the defoliant is released from the microcapsule upon illumination with electromagnetic radiation, preferably sunlight or ambient indoor light, include but are not limited to copper naphthenates 5-ethoxy-3-trichloromethyl-1,2,4-thiadiazole, and O-ethyl S,S-diphenyl phosphorodithioate.

Insect Repellents

Particular embodiments of insect repellant useful for preparing microencapsulated embodiments thereof according to the methods of the invention, wherein the insect repellant is released from the microcapsule upon illumination with electromagnetic radiation, preferably sunlight or ambient indoor light, include but are not limited to 6-butoxycarbonyl-2,3-dihydro-2,2-dimethylpyran-4-one, N,N-diethyl-m-toluamide, dibutylphthalatedibutyl, succinate, 1,5a,6,9,9a,9b-hexahydro-4-a(4H)-dibenzofurancarboxaldehyde, and dipropylpyridine-2,5-dicarboxylate.

Drugs

Particular embodiments of a drug useful for preparing microencapsulated embodiments thereof according to the methods of the invention, wherein the drug is released from the microcapsule upon illumination with electromagnetic radiation, preferably sunlight or ambient indoor light, include but are not limited to ibuprofen, erythromycin, vasopressin, insulin, dideoxyinosine, cyclosporin, taxol, heparin, halofantrine, ethopropazine, griseofulvin, propofol, furosemide, carbamazepine, diazepam, candesartan and cilexetil.

B. Prepolymers

The microcapsules of the invention comprise photoactivatable and non-photoactive (or non-photoactivatable) prepolymers. It will be recognized that the proportion of photoactivatable and non-photoactive prepolymers in the microcapsules will influence the performance of the microcapsules. Specifically, the degree of crosslinking of the prepolymers, the percentage of photoactivatable prepolymer in the prepolymer mixture used to prepare the microcapsules, and the nature of the liquid core will all influence the rate of release of the liquid material once the shell has been exposed to light. As used herein, it will be understood that incorporation of photoactivatable prepolymers into the polymeric shell of the microcapsule renders said shell to be photoactivatable by the cleavage or rearrangement of chemical bonds in the polymeric shell at sites defined or determined by incorporation of a photoactivatable prepolymer molecule or plurality thereof.

Nonphotoactive prepolymers suitable to the present invention can be but are not limited to partially etherified urea-formaldehyde prepolymers, amino acid prepolymers, lactone prepolymers, ester prepolymers with a high solubility in the organic phase and a low solubility in water. Specific examples of non-photoactive prepolymers useful in the practice of the invention include but are not limited to:

2-(1-Naphthyloxy) Ethanol, 2-(1-Naphthyloxy)-Ethyl Acrylate, 2-(2-Naphthlyloxy) Ethanol, 2-(2-Naphthyloxy)-Ethyl Acrylate, 2-(2-Naphthyloxy)-Ethyl Methacrylate, Acrylamide, 2-Propeneamide, Acrylamide, Methyl 2-Acrylamido-2-Methoxyacetate, 2-Acrylamido-2-Methylpropanesulfonic Acid, mono-Butyl Maleate, N-n-Butylmethacrylamide, N-t-Butylmethacrylamide, n-Butyl Methactylate,iso-Butyl Methacrylate-Butyl Methacrylate, Cyclohexylmethacrylamide, Cyclohexyl Methacrylate, 4-Cyclohexylstyrene, Cyclol Acrylate, Cyclol Methacrylate, Diethyl Ethoxymethylenemalonate, N,N-Dimethylanilin, Dimethyl Benzil Ketal, 2,3-Dimethyl-1,3-Butadiene,N,N-Dimethylmethacrylamide,Epichlorohydrin,1-Chloro-2,3-Epoxypropane, Ethyl 3,3-Diethoxyacrylate, Ethyl 3,3-Dimethylacrylate, Ethyl Vinyl Ketone, Vinyl Ethyl Ketone 1-Penten-3-one, Formaldehyde Diallyl Acetal, Fumaronitrile, Glyceryl Propoxy Triacrylate, Glyceryl Trimethacrylate, Glycidoxypropyltrimethoxysilane, Glycidyl Acrylate, n-Heptyl Acrylate, Acrylic Acid n-Heptyl Ester, n-Heptyl Methacrylate, 3-Hydroxypropionitrile, 2-Hydroxypropyl Acrylate, 2-Hydroxypropyl Methacrylate, N-(Methacryloxyethyl)phthalimide, N-(Methacryloxyethyl)succinimide, 1,9-Nonanediol Diacrylate, 1,9-Nonanediol Dimethacrylate, N-(n-Propyl) Acrylamide, ortho-Phthalic Acid, iso-Phthalic Acid, Dihydrazide, Isophthalic Dihydrazine, iso-Phthalic Acid, 1,3-Benzenedicarboxylic Acid, Phthalic Acid, Mono-2-Acryloxyethyl Ester, tere-Phthalic Acid sublimed, 1,4-Benzenedicarboxylic Acid, Phthalic Anhydride, Polyethylene Glycol 2000 Diacrylate, Polyethylene Glycol 2000 Monomethacrylate, Polyethylene Glycol 200 Dimethacrylate, Polyethylene Glycol 200 Diacrylate, Polyethylene Glycol 400 Diacrylate, Polyethylene Glycol 1000 Diacrylate, Polyethylene Glycol 4000 Diacrylate, Polyethylene Glycol 400 Dimethacrylate, Polyethylene Glycol 600 Dimethacrylate, Polyethylene Glycol 1000 Dimethacrylate, Polyethylene Glycol 4000 Dimethacrylate, Polyethylene Glycol 200 Monoacrylate, Polyethylene Glycol 400 Monoacrylate, Polyethylene Glycol 1000 Monoacrylate, Polyethylene Glycol 2000 Monoacrylate, Polyethylene Glycol 3000 Monoacrylate, Polyethylene Glycol 4000 Monoacrylate, Polyethylene Glycol 8000 Monoacrylate, Polyperfluoroethylene Glycol Dimethacrylate, Polypropylene Glycol 4000 Diacrylate, Polypropylene Glycol 400 Dimethacrylate Polypropylene Glycol 1000 Dimethacrylate, Polypropylene Glycol 2000 Dimethacrylate, Polypropylene Glycol 4000 Dimethacrylate, Polypropylene Glycol 400 Monoacrylate, Polypropylene Glycol 400 Monomethacrylate, iso-Propyl Acrylate, Sorbitol Dimethacrylate, Sorbitol Pentaacrylate, 2,2,2-Trifluoroethyl Methacrylate, 1,1,1-Trimethylolpropane Trimethacrylate, Methacrylate, Vinyl Bromoacetate, Vinyl Propionate, Vinyl Triacetoxy Silane, Triphenylphosphonium Bromide, Vinyl Tris-t-Butoxysilane, and m-Xylenebisacrylamide, Polymers comprising photoactivatable prepolymers suitable for the present invention are characterized by being sensitive to electromagnetic radiation, particularly light, and more particularly sunlight or ambient light, wherein illumination with light causes disruption in intra- or interpolymeric linking or bonding. As a consequence, the porosity of the polymeric shell increases and the amount and rate of diffusion of the encapsulated liquid increases to an extent dependent on the percent composition of the polymeric shell from photoactivatable prepolymers, the sensitivity of said polymers to light, and the extent and intensity of light illumination. These properties of the polymers comprising the polymeric shell of the microcapsules of the invention are dependent upon the quantum yield Φ, which is the number of photocleavages per the number photons absorbed for a particular polymer at a particular wavelength. By varying the nature of the photoactive prepolymer (and hence its quantum yield) and the percent of photoactive prepolymer in the polymerized polymeric shell, one can vary the rate of release of the core liquid for a given illumination at a given wavelength.

Photoactivatable prepolymers suitable for the present invention can be but are not limited to, benzophenones, nitrobenzyl alcohols, and preferably benzoin derivatives. Particular embodiments include but are not limited to an o-nitrobenzoyl derivative, an alpha-keto ester, a benzophenone, a benzyl alcohol, a phenacyl ester, a fluorenecarboxylate, an arylamine, a cinnamyl ester, or a vinylsilane, or combination thereof. Preferred photoactivatable prepolymers are dimethoxy benzoins.

In particulars the photoactivatable prepolymers of the invention have the formula (I):

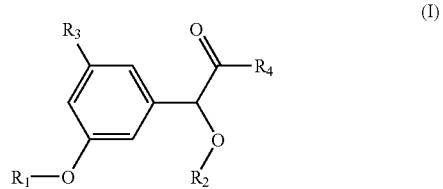

(I)

where:
$R_1$ and $R_2$ are independently hydrogen, alkyl, aryl, alkoxy, substituted alkoxy, hydroxy, amino or carboxy or substituted carboxy, wherein both $R_1$ and $R_2$ are capable of reactions to form polymers and preferably contain hydroxy, amino, carboxy, sulfhydryl or phosphoryl moieties; $R_3$ group is hydrogen, alkoxy, alkyl, aryl, or substituted alkoxy; and $R_4$ is preferable aryl or substituted aryl.

In an embodiment of the present invention, the photoactivatable prepolymers comprise compounds of formula (I) wherein $R_1$ and $R_2$ are substituted alkoxy; $R_3$ is hydrogen or methoxy; and $R_4$ is phenyl.

In another embodiment of the present invention, the photoactivatable prepolymers comprise compounds of formula (I) wherein $R_1$ and $R_2$ are hydroxyalkyl; $R_3$ is hydrogen or methoxy; and $R_4$ is phenyl.

In another embodiment of the present invention, the photoactivatable prepolymers comprise compounds of formula (I) wherein $R_1$ and $R_2$ are $HOCH_2CH_2$—; $R_3$ is hydrogen or methoxy, and $R_4$ is phenyl.

In another embodiment of the present invention, the photoactivatable prepolymers comprise compounds of formula (I) wherein $R_1$ and $R_2$ are $(NZ_1Z_2)$alkyl, wherein $Z_1$ and $Z_2$ are each independently hydrogen, alkyl, alkylcarbonyl, or formyl; $R_3$ is hydrogen or methoxy; and $R_4$ is phenyl.

In another embodiment of the present invention, the photoactivatable prepolymers comprise compounds of formula (I) wherein $R_1$ and $R_2$ are carboxyalkyl; $R_3$ is hydrogen or methoxy; and $R_4$ is phenyl.

In another embodiment of the present invention, the photoactivatable prepolymers comprise compounds of formula (I) wherein $R_1$ and $R_2$ are $(NZ_1Z_2)$carbonylalkyl, wherein $Z_1$ and $Z_2$ are each independently hydrogen, alkyl, alkylcarbonyl, or formyl; $R_3$ is hydrogen or methoxy; and $R_4$ is phenyl.

In another embodiment of the present invention, the photoactivatable prepolymers comprise compounds of formula (I) wherein $R_1$ and $R_2$ are sulfhydrylalkyl; $R_3$ is hydrogen or methoxy; and $R_4$ is phenyl.

In another embodiment of the present invention, the photoactivatable prepolymers comprise compounds of formula (I) wherein $R_1$ and $R_2$ are phosphorylalkyl; $R_3$ is hydrogen or methoxy; and $R_4$ is phenyl.

In another embodiment of the present invention, the photoactivatable prepolymers comprise compounds of formula (I) wherein $R_1$ and $R_2$ are (substituted carbonyl)alkyl; $R_3$ is hydrogen or methoxy; and $R_4$ is phenyl.

DEFINITIONS

As used throughout this specification and the appended claims, the following terms have the following meanings:

As used herein, the term "carboxy" means —COOH or —$COR_{12}$ group, wherein $R_{12}$ is a primary or secondary amino group.

As used herein "carboxyalkyl" means a carboxy group, as defined herein, appended to the parent molecular moiety through an alkyl group, as defined herein.

As used herein, the term "substituted carbonyl" means a —$COR_{13}$ group, where $R_{13}$ is hydrogen, alkyl, aryl, alkyl amine, amine, secondary amine, alkoxy, a biomolecule or a fluorescent label.

As used herein "(substituted carbonyl)alkyl" means a substituted carbonyl group, as defined herein, appended to the parent molecular moiety through an alkyl group, as defined herein.

By "alkyl" or "alkyl group" or grammatical equivalents herein is meant a straight or branched chain alkyl group, with straight chain alkyl groups being preferred. If branched, it may be branched at one or more positions, and unless specified, at any position. Also included within the definition of an alkyl group are cycloalkyl groups such as $C_5$ and $C_6$ rings. In some cases, two R groups may be part of a ring structure, that is, they may be linked to form a cyclic structure, including heterocyclic structures. For example, as described in Pillai, Synthesis, January 1980, pp 1-26, incorporated herein by reference, $R_2$ and $R_3$ may also be similarly joined.

The alkyl group may range from about 1 to 100 carbon atoms ($C_1$-$C_{100}$), with a preferred embodiment utilizing from about 1 to about 20 carbon atoms ($C_1$-$C_{20}$), with about $C_1$ through about $C_5$ being preferred. However, in some embodiments, the allyl group may be larger, particularly if it is a straight chain alkyl. Particularly preferred is methyl in the $R_2$ or $R_3$ positions By "aryl" or "aryl group" herein is meant aromatic rings including phenyl, benzyl, and naphthyl, heterocylic aromatic rings such as pyridine, furan, thiophene, pyrrole, indole and purine, and heterocyclic rings with nitrogen, oxygen, sulfur or phosphorus.

The alkyl and aryl groups may be substituted, for example, a phenyl group may be a substituted phenyl group. Suitable substitution groups include, but are not limited to, alkyl and aryl groups, halogens such as chlorine, bromine and fluorine, amines, carboxylic acids, and nitro groups.

By the term "amine" herein is meant an —$NR_{14}R_{15}$ group. In this embodiment, $R_{14}$ and $R_{15}$ may be the same or different, and may be hydrogen, alkyl or aryl. Primary amines, wherein $R_{14}$ and $R_{15}$ is are both hydrogen, secondary amines, wherein either $R_{14}$ or $R_{15}$ but not both is hydrogen, and tertiary amines, wherein neither $R_{14}$ nor $R_{15}$ is hydrogen are within the scope of these embodiments of the invention, and a preferred —$R_{14}R_{15}$ group is —$NH_2$.

By "hydroxy" herein is meant a —OH group.

As used herein "hydroxyalkyl" means a hydroxy group, as defined herein, appended to the parent molecular moiety through an alkyl group, as defined herein.

By "alkoxy" herein is meant an —$OR_{16}$ group, where $R_{16}$ is an alkyl group as depicted above. Included within the definition of alkoxy is methoxy (—$OCH_3$).

By "substituted alkoxy" herein is meant a —$OXC(R_{17})(R_{18})(R_{19})$ group, wherein X is either not present (i.e. substituted methoxy) or a straight or branched chain alkyl group. In a preferred embodiment, X is a straight chain alkyl group, such that the substituted alkoxy group has the formula —$O(CH_2)_nC(R_{17})(R_{18})(R_{19})$, wherein n is zero (substituted methoxy, which is preferred) or greater, preferably from 1 to 100, with 1 to 20 being especially preferred. $R_{17}$, $R_{18}$ and $R_{19}$ are amino, carboxy, phosphorus-containing moieties, sulfur-containing moieties, protecting groups such as silyl groups and others known in the art, biomolecules, or fluorescent labels. In a preferred embodiment, $R_{17}$ and $R_{18}$ are hydrogen, such that there is a single substitution group.

The term "$NZ_1Z_2$" as used herein, means two groups, $Z_1$ and $Z_2$, which are appended to the parent molecular moiety through a nitrogen atom. $Z_1$ and $Z_2$ are each independently hydrogen, alkyl, alkylcarbonyl, or formyl. Representative examples of $NZ_1Z_2$ include, but are not limited to, amino, methylamino, dimethylamino, diethylamino, acetylamino, and acetylmethylamino.

The term "($NZ_1Z_2$)alkyl" as used herein, means a $NZ_1Z_2$ group, as defined herein above, appended to the parent molecular moiety through an alkyl group, as defined herein. Representative examples of ($NZ_1Z_2$)alkyl include, but are not limited to, aminomethyl, 2-(methylamino)ethyl, 2-(diimethylamino)ethyl, and 3-(ethylmethylamino)propyl.

The term "($NZ_1Z_2$)carbonyl" as used herein, means a $NZ_1Z_2$ group, as defined herein above, appended to the parent molecular moiety through a carbonyl group, as defined herein, Representative examples of ($NZ_1Z_2$)carbonyl include, but are not limited to, aminocarbonyl, (methylamino)carbonyl, (dimethylamino)carbonyl, and (ethylmethylamino)carbonyl.

The term "($NZ_1Z_2$)carbonylalkyl" as used herein) means a ($NZ_1Z_2$)carbonyl group, as defined herein, appended to the parent molecular moiety through an alkyl group, as defined herein.

By "phosphorus containing moiety" herein is meant a functional group containing at least one phosphorus atom. In a preferred embodiment, the phosphorus containing moiety is chemically or functionally active, such that further groups may be attached to the compound using the phosphate. In a preferred embodiment, the phosphorus-containing moiety is a phosphate (—$OPO(OH)_2$ group), pyrophosphates, or a substituted phosphate group of the formula —$OPO(OR_{20})(OR_{21})$. When $R_2$ is a phosphorus containing moiety, it should be understood that the first oxygen attached to the phosphorus atom is the oxygen depicted in the Formulas as attached to $R_2$. In all embodiments, the formation of peroxide groups (—O—O—) is not preferred. In these embodiments, $R_{20}$ and $R_{21}$ include, but are not limited to, hydrogen, alkyl, or aryl. In a preferred embodiment, one of $R_{20}$ and $R_{21}$ is hydrogen. Also included within the definition of phosphorus containing moieties are phosphines (—$R_3P$) (wherein "R" is each independently an alkyl group), and phosphonates (—$RPO(OR_{20})(OR_{21})$).

As used herein "phosphorylalkyl" means a phosphorus containing moiety, as defined herein, appended to the parent molecular moiety through an alkyl group, as defined herein.

By "sulfur containing moiety" herein is meant a functional group containing at least one sulfur atom. As for the phosphates, the sulfur containing moiety is preferably chemically or functionally active, such that further groups such as biomolecules may be attached using the sulfur atom. Thus thiols (—RSH), sulfides (RSR'), sulfoxides (—SO—), sulfones (—$SO_2$—), sulfates (—$OSO_2O$—), and sulfonic acids (—$RSO_2OH$), are all included within the definition of sulfur containing moieties. It should be noted that when the sulfur containing moiety is at the $R_2$ position and is a sulfate, one of the oxygens of the sulfate is the oxygen depicted in the Formulas as attached to $R_2$; that is, a peroxide is not formed.

As used herein "sulfhydrylalkyl" means a sulfur containing moiety, as defined herein, appended to the parent molecular moiety through an alkyl group, as defined herein.

By "halide" herein is meant a halide atom Preferred halides include chlorine, fluorine, bromine and iodine, with chlorine and fluorine being particularly preferred, and chlorine being most preferred.

C. Optional Additives

In addition to the prepolymers (including mixtures of photoreactive and nonphotoreactive embodiments thereof) and the liquid core materials as set forth above, the microcapsules of this invention can comprise certain optional additives. Exemplary optional additives include but are not limited to solvents, polymerization catalysts, wall-modifying agents and light adsorbing additives that alter photoconversion rates and therefore release rates of the microencapsulated fragrance, drug, herbicide, insecticide or other liquid material as set forth herein.

In particular, solvents provide a means for controlling the polymeric wall-forming reaction. An appropriately-selected solvent added to the organic phase can modify characteristics and properties of the organic phase to achieve the most optimum production of microencapsulated embodiments of the liquid materials of the invention. The need for a solvent and the type of solvent needed—inter alia, hydrophobic or hydrophilic—depends on the nature of the liquid core material. Aliphatic and alicyclic solvents are examples of hydrophobic solvents, and alcohols and ketones are examples of hydrophilic solvents. The amount of solvent can be varied as needed to achieve the desired results.

Catalysts capable of enhancing the polymeric wall-forming reaction can be placed in either the aqueous or organic phase, Catalysts are generally used when the core material is too insoluble or immiscible to provide ready mixing with the aqueous phase and hence facilitate the encapsulation reaction. Catalysts such as carboxylic acids and sulfonic acids are particularly useful. Examples include orthochlorobenzoic acid, 2-phenyl-2,2-dichloroacetic acid, benzoic acid, salicylic acid, p-toluenesulfonic acid and dodecylbenzene sulfonic acid. The same catalytic effect can be accomplished by dissolving salts of these acids in the aqueous or organic phase and then acidifying the aqueous phase. The acid form is thus produced by ion exchange.

Polymeric wall-modifying agents serve to modify the character of the microcapsule wall by varying its permeability to the core material. Suitable microcapsule polymeric wall-modifying agents contain a plurality of hydroxyl or mercapto groups capable of reacting with the reactive on the prepolymer. The microcapsule polymeric wall modifier can be used in the organic solution to add multiple linkages to the methylol groups, inter alia, to increase the degree of cross-linking, or to exhaust active sites on the prepolymer to decrease the degree of cross-linking. Thus, depending on the kind of modifier used and the ratio of modifier to prepolymer, the permeability of the microcapsule polymeric wall (and consequently the release rate of the core liquid) can be either increased or decreased. Castor oil is one example of such an agent. The preferred cross-linking microcapsule polymeric wall-modifying agent is pentaerythritol tetrakis (mercaptopropionate), commercially-available under the tradename Mercaptate Q-43 Ester (Cincinnati Milacron Chemicals, OH). Other poly-functional mercaptan esters having similar properties can be used.

Light adsorbing additives serve to change the photoresponsive properties of the final microcapsules by absorbing electromagnetic radiation that would normally activate the photoresponsive polymers. This imparts the final microcapsules with variable responses to light. These additives include but are not limited to conventional sunscreen agents such as octyl methoxycinnamate (OMC), ethylhexyl p-methoxycinnamate, octyl salicylate (OCS), para-aminobenzoic acid (PABA), octyl dimethyl PABA, octocrylene, zinc oxide, or titanium dioxide D. Emulsion Formation In the practice of the inventive methods of this invention, once the organic solution comprising the core liquid is provided, an emulsion is formed by dispersing the organic solution in an aqueous solution comprising water and a surface-active agent. The relative quantities of organic and aqueous phase are not determinative to the operable practice of the inventions and can vary over a wide range, limited mostly by convenience and ease of handling. In practical usage, the organic phase will comprise a maximum of about 55% by volume of the total emulsion and will comprise discrete droplets of organic solution dispersed in the aqueous solution.

The surface-active agent can be any of the wide variety of compounds known to be useful for lowering the surface tension of a fluid interface. Both nonionic and anionic types of such agents are useful Examples of nonionic surface-active agents are long chain alkyl and mercaptan polyethoxy alcohols, alkylaryl polyethoxy alcohols, alkylaryl polyether alcohols, allyl polyether alcohols, polyoxyethylene sorbitan fatty acid esters, polyoxyethylene ethers, and polyethylene glycol esters with fatty or rosin acids. Examples of anionic surface-active agents are calcium, amine, alkanolamine, and alkali metal salts of alkyl and alkylaryl sulfonates, vegetable sulfonates; and ethoxylated and propoxylated mono- and diethers of phosphoric acid. Blends of surface-active agents are also useful in the practice of the inventive methods. Preferred surface-active agents are polyethylene glycol ethers of linear alcohols and alkali metal salts of alkyl and alkylaryl sulfonates.

The quantity of surface-active agent is not critical to the invention, and can vary over a wide range. For convenience, the agent generally comprises from about 0.1% to about 5.0% by weight of the aqueous phase. The agent can be added before or after the emulsion is formed.

In some systems, emulsion stability can be enhanced by adding a protective colloid to the aqueous phase. A protective colloid stabilizes a dispersed system against aggregation, flocculation, and coalescense. Many materials are known to function as protective colloids and are available commercially, including polyvinyl alcohols, alginates, alpha- and gamma protein, casein, methyl cellulose, carboxymethyl cellulose, gelatin, glues, natural gums, polyacids, and starch. The colloid can be added to the aqueous phase prior to the formation of the emulsion, or to the emulsion itself after it has been formed. Although the colloid is an optional additive, its inclusion in the present system is preferred. Polyvinyl alcohol protective colloids are particularly preferred.

Additional compounds which serve as protective colloids are the salts of lignin sulfonate, including sodium, potassium, magnesium, calcium or ammonium salts. Among commercial lignin sulfonates are Treax®, LTS, LTK and LTM, respectively, potassium, magnesium and sodium salts of lignosulfonate (50% aqueous solutions; Scott Paper Co., Forest Chemical Products); Marasperse CR®, and Marasperse CBOS-3®, sodium lignosulfonate (American Can Co.); Polyfon O®, Polyfon T®, Reax 88B®, Reax 85B®, sodium salts of lignin sulfonate and Reax C-21®, calcium salt of lignin sulfonate (Westvaco Polychemicals); Orzan S and Orzan A, the sodium and ammonium salts of lignosulfonate (ITT Rayonier, Inc.).

The actual quantity of colloid is not critical and any amount that is effective in enhancing emulsion stability can be used. It is most convenient to use between about 0.1% and about 5.0% colloid by weight (relative to the aqueous phase).

The droplet size in the emulsion is also not a critical feature of the invention. For greatest utility of the final product, the droplet size will fall in the range of about 0.5 microns to about 4000 microns in diameter. The preferred range for most applications is from about 1 micron to about 100 microns in diameter. The emulsion is advantageously prepared using any conventional high shear stirring device. Once the desired droplet size is attained, mild agitation is generally sufficient to prevent droplet growth throughout the balance of the process.

E. Microparticle Polymeric Wall Formation

Once the dispersion and desired droplet size are attained, the emulsion is activated to initiate polymerization.

Polymerization initiation is accomplished by self-condensation performed at a pH of between about 1.0 and about 12.0 and at a temperature of between about 10 degrees C. and about 100 degrees C. It will be recognized in the art that evaporation of the liquid components is preferably avoided, and that at temperatures at or near the evaporation point of a liquid component pressure is applied to counteract any evaporation. Initiation can occur either by chemical or radical initiation but the preferred embodiment is chemical initiation.

As the polymer wall becomes more rigid, contact between the active groups on the prepolymer becomes increasingly more difficult. Thus, the in situ self-condensation polymerization reaction is self-terminating and is generally allowed to run to completion. The reaction can be arrested before completion and in this manner, microcapsule polymeric wall tightness, rigidity, and permeability can be controlled. This can also be accomplished in most cases by a wall modifier as described above. The timing of polymerization arrest to achieve a particular microcapsule polymeric wall tightness, rigidity, and permeability that can be determined empirically as will be understood by those of ordinary skill in the art. Methods for making such determinations include gas chromatographic (GC) analysis of release rate in the presence and absence of light, susceptibility to shear forces and compression. Such methods are well known to those practiced in the art. (see, for example, Deasy, 1984, MICROENCAPSULATION AND RELATLED DRUG PROCESSES, New York: M. Dekker).

Once the microcapsules are formed, they can be stored and used as an aqueous dispersion, or filtered and recovered as dried capsules. In either form, the capsules are useful and effective in the slow or no release of the core liquid until activated by electromagnetic radiation, particularly sunlight or ambient indoor light. Dispersions are preferably stabilized by dispersants dissolved in the continuous phase and maintained in the dark, or in light-reducing or eliminating containers known in the art (e.g., brown bottles or other light-reducing or opaque packaging). Any conventional dispersant can be used, including but not limited to lignin sulfonates, polymeric alkylnaphthalene sulfonates, sodium naphthalene sulfonate, polymethylene bis-naphthalene sulfonate, and sodium-N-methyl N-(long chain acid) taurates.

The invention thus provides microcapsules having solid nonporous polymeric shells enclosing organic phase droplets wherein the nonporous polymer comprises photoactivatable prepolymers that render the microcapsule susceptible to electromagnetic radiation, particularly sunlight and ambient indoor light. Illumination of the microcapsules of the invention renders the microcapsule more permeable to the encapsulated liquid material, thereby releasing the liquid material from the microcapsule.

In the examples set forth herein, the organic phase contains a fragrance, and different microcapsule polymer compositions result in different release rates of fragrances upon exposure to light. This enables a perfume, for example, to change from one predominant smell to another during the course of light exposure.

The following examples and reaction schemes are offered as illustrative of both the materials, the process using the materials, and uses of the present invention, and are intended neither to define nor limit the invention in any manner.

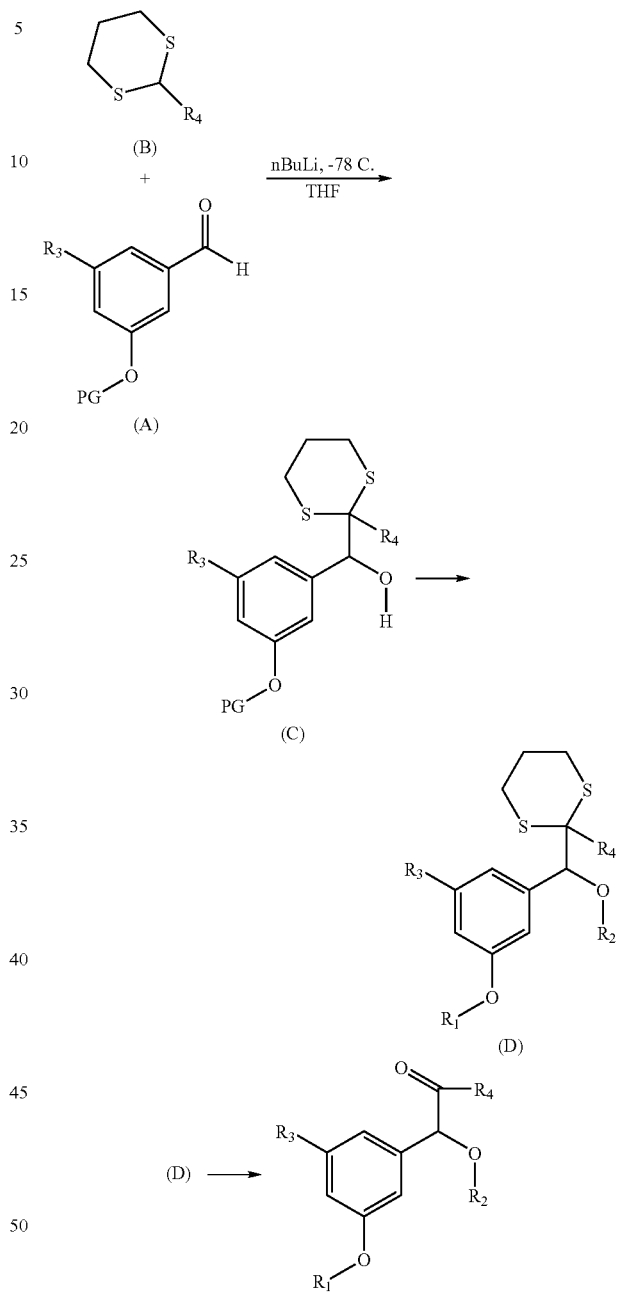

Compounds of the present invention can be prepared as described in Scheme 1. Benzaldehydes of formula (A), wherein PG is a hydroxy protecting group and $R_3$ is hydrogen, alkoxy, alkyl, aryl, or substituted alkoxy, can be treated with 1,3-dithianes of formula (B), wherein $R_4$ is aryl or substituted aryl, and an organolithium reagent, such as, but not limited to, n-butyllithium, to provide compounds of formula (C). Compounds of formula (C) can be deprotected and then treated with a base and an alkylating agent, wherein the alkylating agent contains a hydroxy, amino, carboxy, sulfhydryl or phosphoryl moiety, to provide compounds of formula (D). It is to be understood that this step can be accomplished in a stepwise fashion. For example, compounds of formula (C) can be treated with the alkylating agent and optionally isolated. The alkylated compound can then be deprotected, optionally isolated, and treated with an alkylating agent to provide compounds of formula (D). Compounds of formula (D) can be treated with reagents that cleave 1,3-dithianes, such as, but not limited to, mercuric perchlorate, to provide compounds of the present invention wherein $R_1$ and $R_2$ are independently hydrogen, alkyl, aryl, alkoxy, substituted alkoxy, hydroxy, amino or carboxy or substituted carboxy, wherein both $R_1$ and $R_2$ are capable of reactions to form polymers and preferably contain hydroxy, amino, carboxy, sulfhydryl or phosphoryl moieties.

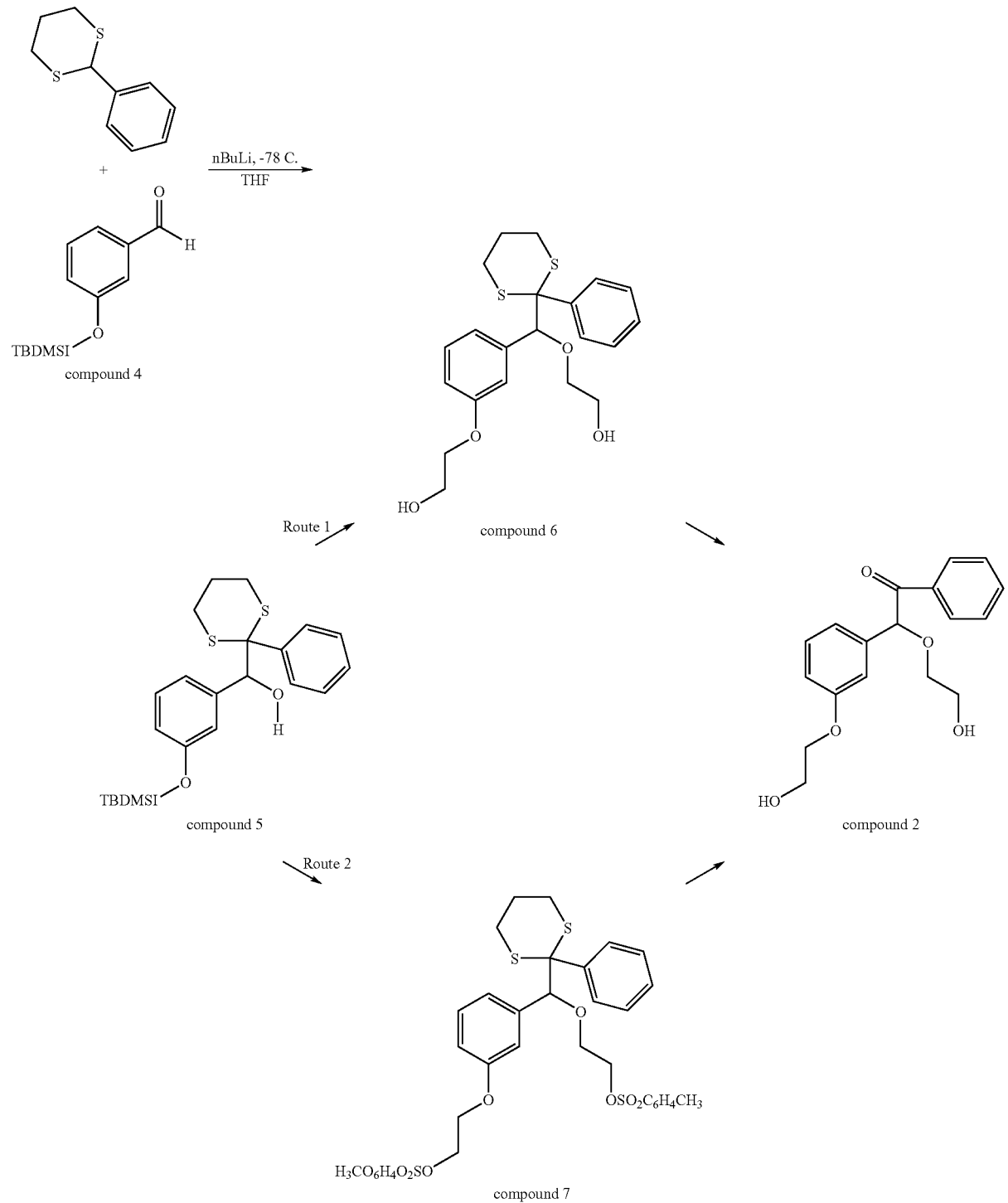

Synthesis of 3-(tert-Butyldimethylsilyloxy)benzaldehyde (Compound 4)

To a solution of 3-hydroxybenzaldehyde (12.21 g, 100 mmol) in 600 mL THF was added tert-butyldimethylsilyl chloride (TBDMSCl, 18.84 g, 125 mmol). The solution was cooled to 0° C. and triethylamine (12.65 g, 17.4 mL, 125 mmol) was added dropwise. The reaction mixture was brought to room temperature and stirred 5 h. The mixture was filtered and the THF removed under reduced pressure. The oil was repeatedly dissolved in 200 mL portions of THF and evaporated, until no more triethylamine hydrochloride precipitated. The oil was then dissolved in 150 mL diethyl ether, filtered through a plug of neutral alumina and activated charcoal to remove the salt and the yellow color, and evaporated. The colorless, mobile oil was dried in vacuo overnight. Yield: 21.43 g (91%). IR: 1703, 1583, 1482, 1278, 1145, 840 cm-1. 1H NMR (CDCl3, TMS) δ 9.927 (s, 1H), 7.447 (d, J) 7.50 Hz, 1H), 7.379-7-335 (m, 2H), 7.096-7.074 (m, 1H), 0.994 (s, 9H), 0.215 (s, 6H). 13C NMR (CDCl3, TMS) δ 191.60, 156.34, 138.03, 130.03, 126.34, 123.46, 119.70, 25, 59, 18.12, −4.52. Anal. Calcd. for Cl3H20O2Si: C, 66.05; H, 8.53. Found: C, 66.13; H, 8.53.

Synthesis of (±)-1-Hydroxy-1-[3-(tert-butyldimethylsilyloxy)phenyl]-2-phenyl-2-(1,3-dithian-2-yl) ethane (Compound 5)

The title compound was prepared as disclosed in U.S. Pat. Nos. 5,767,288 and 6,280,711, incorporated by reference) A solution of 2-phenyl-1,3-dithiane (15.71 g, 80 mmol) in 125 ml, of THF was prepared. The solution was treated at 0° C. under a nitrogen atmosphere with 40 mL of n-butyllithium (2.0 M in cyclohexane, 80 mmol). After 30 min, 4 (18.91 g, 80 mmol) was added. The solution was stirred for 1 h at 0° C. and then poured into 100 mL of 1 N HCl and extracted with methylene chloride (4×50 mL). The organic phase was washed with brine, dried with Mg₂SO₄, filtered through a plug of activated charcoal and silica gel, and evaporated under reduced pressure. The resulting oil was crystallized from ethanol/water to form a white powder. Yield: 28.98 g (84%). Mp 75-76° C. IR: 3449 (br), 1601, 1484, 1275, 1152, 834 cm-1. $^1$H NMR (CDCl3, TMS) δ 7.70 (d, J) 7.50 Hz, 2H), 7.308-7.235 (m, 3H), 6.937 (t, J) 7.79 Hz, 1H), 6.682-6.660 (m, 1H), 6.427-6.404 (m, 2H), 4.926 (d, J) 3.73 Hz, 1H), 2.936 (d, J) 3.76 Hz, 1H), 2.739-2.610 (m, 4H), 1.942-1.879 (m, 2H), 0.935 (s, 9H), 0.111 (s, 6H). $^{13}$C NMR (CDCl3, TMS) δ 154.43, 138.89, 137.47, 130.42, 128.00, 127.69, 127.36, 121.23, 119.89, 119.54, 80.74, 66.36, 27.22, 26.93, 25.65, 24.69, 18.03, −4.40. Anal. Calcd. C23H32O2S2Si: C, 63.84; H, 7.45. Found: C, 63.83; H, 7.26.

Synthesis of (±)-1-(Ethoxy-2-hydroxy)-1-[3-(ethoxy-2-hydroxy)phenyl]-2-phenyl-2-(1,3-dithian-2-yl) ethane (Compound 6) (Route 1)

A solution of 2-phenyl-1,3-dithiane (1.57 g, 8 mmol) in 15 mL of THF was prepared. The solution was treated at 0° C. under a nitrogen atmosphere with 4 mL of n-butyllithium (2.0 M in cyclohexane, 8 mmol). After 30 min, 4 (1.9 g, 8 mmol) was added. The solution was stirred for 1 h at 0° C. and then ethylene oxide (0.5 g, 14 mmol) was added drop wise via canula and the solution was allowed to stir for 1 h at 0° C. The solution was then treated with 1 M TBAF in THF (8.8 mL, 8.8 mmol) dropwise via canula and allowed to stir for 1 h. To this solution was added ethylene oxide (0.5 g, 14 mmol) via canula. The solution was allowed to react overnight and then poured into 100 mL of 1 N HCl and extracted with methylene chloride (4×50 mL). The organic phase was washed with brine, dried with Mg₂SO₄, filtered through a plug of activated charcoal and silica gel, and evaporated under reduced pressure The resultant oil was purified on silica gel, Yield 1.8 grams (57%).

Synthesis of (±)-1-(Ethoxy-2-hydroxy)-1-[3-(ethoxy-2-hydroxy)phenyl]-2-phenyl-2-(1,3-dithian-2-yl) ethane (Compound 6) (Route 2)

A solution of 2-phenyl-1,3-dithiane (1.57 g, 8 mmol) in 15 mL, of THF was prepared. The solution was treated at 0° C. under a nitrogen atmosphere with 4 mL of n-butyllithium (2.0 M in cyclohexane, 8 mmol). After 30 min, 4 (1.9 g, 8 mmol) was added. The solution was stirred for 1 h at 0° C. and then ethylene carbonate dissolved in dry THF (0.7 g. 9 mmol, 2 mL) was added drop wise via syringe. The solution was stirred for 1 h at 0° C. and then poured into 100 mL of 1 N HCl and extracted with methylene chloride (4×50 mL). The organic phase was washed with brine, dried with Mg₂SO₄, filtered through a plug of activated charcoal and silica gel, and evaporated under reduced pressure. The resulting oil was dissolved in 15 mL of dry THF under a dry nitrogen atmosphere Ethylene carbonate dissolved in dry THF (0.7 g. 9 mmol, 2 mL) was added and the solution cooled to 0° C. The solution was treated with 1 M TBAF in THF (88 mL, 8.8 mmol) dropwise. The solution was allowed to react overnight and then was poured into ethyl acetate (50 mL) and washed with water (5×50 mL). The organic phase was dried with Mg₂SO₄ and evaporated. The residue was dissolved in 200 mL of diethyl ether, filtered through a small quantity of neutral alumina and activated charcoal, and dried in vacuo, Yield 2.3 grams (72%).

Synthesis of (±)-1-(Ethyl-2-p-toluenesulfonate)-1-[3-(ethyl-2-p-toluenesulfonate) phenyl]-2-phenyl-2-(1,3-dithian-2-yl)ethane (Compound 7)

A solution of compound 5 (2.8 g, 6.5 mmol) and 2-bromoethyl-p-toluenesulfonate (2.1 g, 8 mmol) in 15 mL of dry THF was prepared under a dry nitrogen atmosphere. The solution was treated with 1 M TBAF in THF (6.8 mL, 6.8 mmol) dropwise. The solution was allowed to react overnight and then was poured into ethyl acetate (50 mL) and washed with water (5×50 mL) The organic phase was dried with Mg₂SO₄ and evaporated. The residue was dissolved in 20 mL of diethyl ether, filtered through a small quantity of neutral alumina and activated charcoal, and dried in vacuo. The residue was dissolved in 50 mL of THF under a dry nitrogen atmosphere. The solution was cooled to −78° C., and n-butyllithium (2.0 M in cyclohexane, 4 mL, 8 mmol). To this solution was added 2-bromoethyl-p-toluenesulfonate (2.1 g, 8 mmol) in 15 mL of dry THF and the cold bath was removed. After 1 h, reaction was poured into 1N HCl and extracted with ethyl acetate. The organic phase was dried and evaporated under reduced pressure. The resulting compound was not further characterized.

General Deprotection Procedure and Synthesis of (±)-O-(Ethoxy-2-hydroxy)-3'-(ethoxy-2-hydroxy) benzoin (Compound 2)

To a solution of Compound 6 or 7 (0.25 mmol) in 5 ml 9:1 (v/v) acetonitrile/water was added mercuric perchlorate (0.33 mmol). The solution was stirred for 15 min, filtered through a 0.45 μm PTFE syringe filter into a 5% sodium bicarbonate solution (10 mL), and extracted with 50 mL of methylene chloride. The organic phase was dried and evaporated under reduced pressure to yield a colorless oil. Samples for analysis were evaporated from methanol, dissolved in warm water, and lyophilized. Typical yield: ~0.2 mmol (80%). 1H NMR (CDCl3, TMS) δ, 7.629 (m, J=7.55 Hz, 2H), 7.41-7.27 (m, 3H), 7-18 (t, 1H), 6.91 (s, 1H) 6.87 (m, 1H), 6.77 (m, 1H), 6.07 (s, 1H), 4.15-4.05 (m, 2H), 4.03-0.96 (m, 4H), 3.84 (m, 2H), 2.28 (d, 1H), 2.08 (d, 1H).

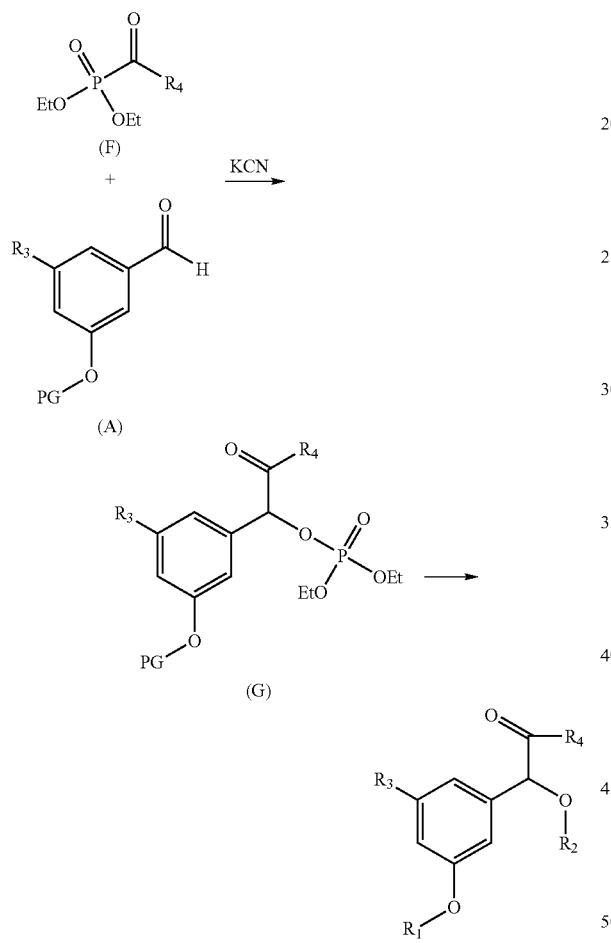

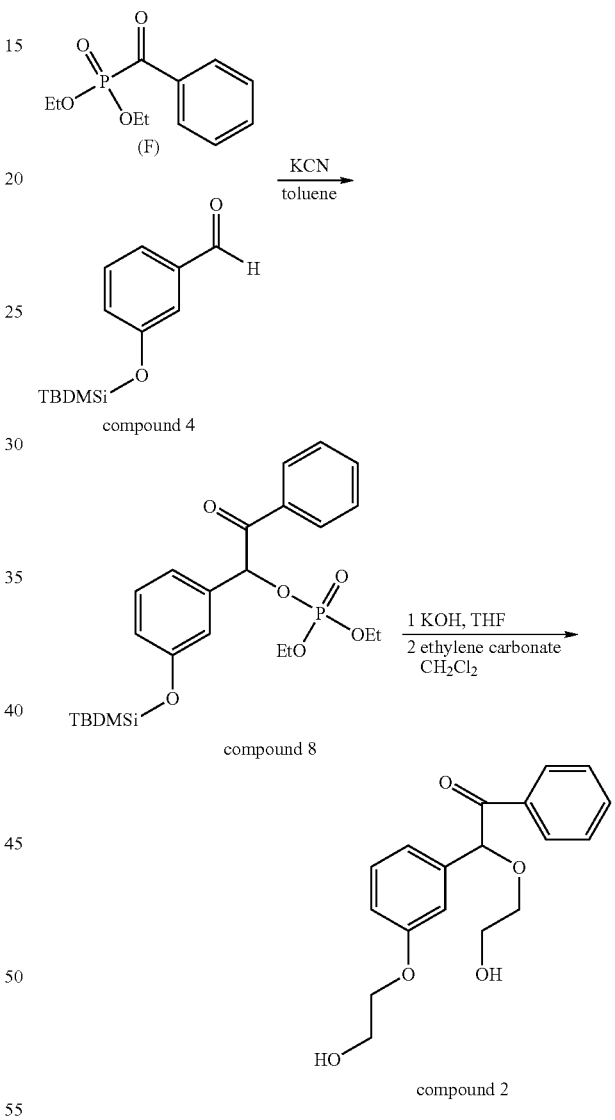

Compounds of the present invention can be prepared as described in Scheme 3. Benzaldehydes of formula (A), wherein PG is a hydroxy protecting group and $R_3$ is hydrogen, alkoxy, alkyl, aryl, or substituted alkoxy, can be treated with KCN and phosphonic acid diethyl esters of formula (F), wherein $R_4$ is aryl or substituted aryl, to provide phosphonates of formula (G). Compounds of formula (G) can be deprotected and treated with a base and an alkylating agent, wherein the alkylating agent contains a hydroxy, amino, carboxy, sulfhydryl or phosphoryl moiety, to provide compounds of the present invention. It is to be understood that this step can be accomplished in a stepwise fashion. For example, compounds of formula (G) can be subjected to conditions that only remove the PG group, optionally isolated, and treated with an alkylating agent, optionally isolated, and subject to conditions that remove the —P(O)(OEt)$_2$ group, optionally isolated, and treated with an alkylating agent to provide compounds of the present invention wherein $R_1$ and $R_2$ are independently hydrogen, alkyl, aryl, alkoxy, substituted alkoxy, hydroxy, amino or carboxy or substituted carboxy, wherein both $R_1$ and $R_2$ are capable of reactions to form polymers and preferably contain hydroxy, amino, carboxy, sulfhydryl or phosphoryl moieties.

Synthesis of (±)-diethyl 1-(3-tert-butyldimethylsilyloxyphenyl)-2-oxo-2-phenylethyl Phosphate (Compound 8)

Following the method of Demir et al. (*J. Org. Chem.* 2005, 70, 10584-10587) a solution of Compound 4 (1.9 g, 8 mmol) and benzoyl-phosphonic acid diethyl ester (1.9 g, 8 mmol) were dissolved in dry DMF (50 mL). To this solution was added KCN (52 mg, 0.8 mmol). The solution was stirred for 1 h at 0° C. and then poured into 100 mL of 1 N HCl and extracted with methylene chloride (4×50 mL). The organic phase was washed with brine, dried with $Mg_2SO_4$, filtered through a plug of activated charcoal and silica gel, and evaporated under reduced pressure to yield 88% of compound 8.

Synthesis of (±)-2-(2-hydroxyethoxy)-2-[3-(2-hydroxyethoxy)phenyl]-1-phenylethanone (Compound 2)

To a solution of Compound 8 (0.25 mmol) in 10 mL of THF was added 0.55 mmol of KOH. The solution was heated to reflux and was stirred for 15 mm, poured into 10 mL of 1 N HCl and extracted with methylene chloride (4×50 mL). The organic phase was washed with brine, dried with $Mg_2SO_4$, filtered through a plug of activated charcoal and silica gel, and evaporated under reduced pressure. The resulting oil was dissolved in 15 mL of dry THF under a dry nitrogen atmosphere and ethylene carbonate dissolved in dry THF (80 mg, 1 mmol) was added and the solution cooled to 0° C. To this solution with rapid stirring was added dry pyridine (0.5 mmol). The solution was stirred for, 1 hour and then poured into 10 mL of 1 N HCl and extracted with methylene chloride (4×50 mL). The organic phase was washed with brine, dried with $Mg_2SO_4$, filtered through a plug of activated charcoal and silica gel, and evaporated under reduced pressure. Overall yield: ~0.08 mmol (35%). 1H NMR (CDCl3, TMS) δ, 7.629 (m, J 7.55 Hz, 2H), 7.41-7.27 (m, 3H), 7.18 (t, 1H), 6.91 (s, 1H) 6.87 (m, 1H), 6.77 (m, 1H), 6.07 (s, 1H), 4.15-4.05 (m, 2H), 4.03-3.96 (m, 4H), 3.84 (m, 2H), 2.28 (d, 1H), 2.08 (d, 1H).

Synthesis of (+−)3-[1-(2-aminoethoxy)-2-oxo-2-phenylethyl]Phenoxy Acetic Acid Compound 1

Compound 5 is selectively alkylated at the phenolic hydroxyl in dry tetrahydrofuran (THF) under a nitrogen atmosphere by treatment with tetrabutylammonium fluoride (TBAF) in the presence of methyl bromoacetate. A solution containing 50 mmols of the TBDMS ester of the parent compound is treated with 1 M TBAF in 150 mL THF (68.25 mL, 68.25 mmol) dropwise. The solution is allowed to react overnight, then is poured into ethyl acetate (200 mL) and washed with water (5-fold, 50 mL aliquots). The organic phase is dried with $Mg_2SO_4$ and evaporated. The residue is dissolved in 200 mL diethyl ether, filtered through a small quantity of neutral alumina and activated charcoal, and dried in vacuo. The product is crystallized from ethyl acetate/hexanes, to afford a white powder. This powder is treated with N-(2-bromoethyl)phthalamide in THF and subsequent hydrazinolysis. The organic phase is dried with $Mg_2SO_4$ and evaporated. The residue is dissolved in 200 ml diethyl ether, filtered through a small quantity of neutral alumina and activated charcoal, and dried in vacuo. The methyl ester product is crystallized from ethyl acetate/hexanes, to afford a white powder.

Photoactivatable prepolymers prepared as described above (or other analogous or equivalent prepolymers prepared according to the ordinary skill in the art) can be used to prepare microcapsules of the invention according to the following Examples, which are not intended to be limiting.

Example 1

Microencapsulation of Cyclohexyl Ethyl Acetate with 1% Photoactivatable Prepolymer (Compound 2)

An aqueous solution was prepared, comprising 0.3% Tergitol (a surfactant) and 5% NaOH. In a separate vessel, 100 g of cyclohexyl ethyl acetate (a common fragrance), 50 g of Bisphenol-A liquid epoxy resin (Dupont), and 1 g of photoactivatable prepolymer (Compound 2) were mixed. The fragrance/prepolymer solution was added to the aqueous solution and an emulsion formed by means of a high shear stirrer, the organic solution forming a dispersed phase with droplets ranging in size from 5 to 20 microns in diameter as determined by electron microscopy. Mild agitation was maintained as the temperature was raised to 50 degrees Celsius for three hours. The resulting suspension was then allowed to cool to room temperature and the pH adjusted to 7. Observation of the suspension under both a laboratory microscope and an electron microscope revealed discrete, roughly spherical, fully enclosed microcapsules with smooth-surfaced outer walls.

Example 2

Microencapsulation of Andrane with 1% Photoactivatable Prepolymer (Compound 2)

An aqueous solution was prepared, comprising 0.7% Brij-35 (a surfactant) and 5% NaOH. In a separate vessel, 100 g of Andrane (a common fragrance), 50 g of Bisphenol-A liquid epoxy resin (Dupont), and 1 g of photoactivatable prepolymer 2 were mixed. The fragrance/prepolymer solution was added to the aqueous solution and an emulsion formed by means of a high shear stirrer, the organic solution forming the dispersed phase with droplets ranging in size from 5 to 20 microns in diameter as determined by electron microscopy. Mild agitation was maintained as the temperature was raised to 50 degrees Celsius for three hours. The resulting suspension was then allowed to cool to room temperature and the pH adjusted to 7, and the microcapsules recovered.

The descriptions of particular embodiments of the microcapsules and methods for producing them embodied above are intended to be representative of and not limiting to the invention. Although the reagents and methods of this invention have been described in terms of preferred embodiments, it will be apparent to those skilled in the art that alternative implementations, compositions and/or methods herein described can be made without departing from the concept, spirit and scope of the invention. All such similar substitutes and modifications apparent to those skilled in the art are deemed to be within the scope and spirit of the invention as defined by the appended claims.

I claim:

1. A method for producing microcapsules comprising a substantially water-insoluble liquid material within a non-porous, light-sensitive shell, wherein the non-porous shell is characterized by a release rate of the liquid material in the absence of light of less than 1 ppm/minute, wherein exposure to light converts the nonporous shell into a porous shell characterized by a release rate of the liquid material of from 1 to at least 100 ppm/minute, the method comprising the steps of:
(a) providing an organic solution comprising said liquid material and a photoactivatable prepolymer or mixture of a photoactivatable prepolymer and a nonphotoactive-based prepolymers dissolved therein, wherein the photoactivatable prepolvmer is selected from the group consisting of (+/−)3-[1-(2-aminoethoxy)-2-oxo-2-phenylethyl] phenoxy acetic acid, 2-(2-hydroxyethoxy)-2-[3-(2-hydroxyethoxy)-5-methylphenyl]-1-phenylethanone, and photoactivatable combinations thereof;
(b) creating an emulsion of said organic solution in a continuous phase aqueous solution comprising water and a surface-active agent, wherein said emulsion comprises discrete droplets of said organic solution dispersed in said continuous phase aqueous solution, there being formed thereby an interface between the discrete droplets of organic solution and the surrounding continuous phase aqueous solution; and (c) causing in situ self-condensation and curing of said prepolymers in the organic phase of said discrete droplets adjacent to said interface by catalysis using heat, pH, or a chemical or free radical initiator for a time sufficient to allow substantial completion of in situ condensation of said prepolymers, thereby converting the liquid droplets of said organic solution to microcapsules comprising a solid nonpermeable polymer shell that encloses said liquid material.

2. A method according to claim 1, wherein the prepolymer of step (a) comprises from about 1% to about 70% of the organic solution on a weight basis.

3. A method according to claim 1, wherein the droplets of the dispersion formed in step (b) are from about 0.5 microns to about 4000 microns in diameter.

4. A method according to claim 1, wherein the in situ self-condensation in step (c) is performed at a pH of between about 1.0 and about 12.0.

5. A method according to claim 1, wherein the in situ self-condensation in step (c) is performed at a temperature between about 10 degrees C. and about 100 degrees C.

6. A method according to claim 1, wherein said organic solution contains a wall-modifying agent which serves to modify the character of the microcapsule polymeric wall by varying its permeability to the core material.

7. A method according to claim 1, wherein the liquid material comprises a fragrance, a flavor, a drug, an herbicide or a pesticide.

8. A method according to claim 1, wherein the liquid material comprises a plurality of substantially water-insoluble compounds that are fragrances, flavorings, drugs, herbicides or pesticides.

* * * * *